United States Patent [19]
Pera

[11] Patent Number: 5,944,012
[45] Date of Patent: *Aug. 31, 1999

[54] METHOD FOR DISPENSING ANTIOXIDANT VITAMINS BY INHALATION BACKGROUND OF THE INVENTION

[76] Inventor: Ivo E. Pera, P.O. Box 9224, Hollywood, Fla. 33384

[ * ] Notice: This patent is subject to a terminal disclaimer.

[21] Appl. No.: 08/852,331

[22] Filed: May 7, 1997

Related U.S. Application Data

[63] Continuation of application No. 08/621,428, Mar. 25, 1996, abandoned.

[51] Int. Cl.⁶ .................................................. A61M 15/00
[52] U.S. Cl. ............................. 128/203.15; 128/203.12; 128/203.21
[58] Field of Search ..................... 128/203.15, 203.12, 128/203.21, 203.23, 200.14, 200.24; 604/58

[56] References Cited

U.S. PATENT DOCUMENTS

| | | | |
|---|---|---|---|
| 5,075,116 | 12/1991 | Lattaye et al. | 424/617 |
| 5,308,874 | 5/1994 | Sanchez et al. | 514/731 |
| 5,349,947 | 9/1994 | Newshoule et al. | 128/203.15 |
| 5,642,728 | 7/1997 | Andersson et al. | 128/203.15 |
| 5,655,523 | 8/1997 | Hodson et al. | 128/203.15 |
| 5,669,398 | 9/1997 | Pera et al. | 128/203.15 |

*Primary Examiner*—John G. Weiss
*Assistant Examiner*—V. Srivastava
*Attorney, Agent, or Firm*—Malin, Haley, DiMaggio & Crosby

[57] ABSTRACT

A method is provided for dispensing dry powder antioxidant compounds, preferably consisting of vitamin C, vitamin E, betacarotene and a membrane permeation enhancer such as lactose. The compound is administered via a conventional dry powder inhaler to deliver said the compound into the subject's respiratory tract in order to enhance prophylactic and therapeutic effects of the antioxidant vitamins. Other antioxidant vitamins can also be included within the dry powder compound.

13 Claims, No Drawings

METHOD FOR DISPENSING ANTIOXIDANT VITAMINS BY INHALATION BACKGROUND OF THE INVENTION

This application is a continuation of U.S. application Ser. No. 08/621,428 filed Mar. 25, 1996 now abandoned.

BACKGROUND OF THE INVENTION

1. Field of the Invention

The present invention relates generally to medical procedures and particularly to a method for dispensing antioxidant vitamins as a therapeutic treatment of diseases of the respiratory tract.

2. Description of the Prior Art

The assimilation of an adequate quantity of physiologically important antioxidant vitamins are essential to the health of people. Failure of the body to assimilate the necessary amount of such antioxidant vitamins which prevent free radicals to damage the body functions can lead to improper functioning of the metabolic processes, as well as to a variety of diseases and associated symptoms. For example, deficiency of betacarotene increases susceptibility to microbial infections, xerophthalmia and other eye disorders, loss of appetite and weight, sterility, abnormalities of nerve and epithelial connective tissue and of bones.

Deficiency of vitamin C can cause a breakdown of intercellular collagen substance, bleeding, petechide, fragility of the walls of capillaries, brittle bones which cease to grow, keratoconjunctivitis sicca, xerostomia, salivary gland enlargement, xerosis, hyperpigmentation, ictyosis, neuropathies and mental depression. While antioxidant vitamin deficiencies are often associated with improper dietary intake, they are also likely to be the result of malabsorption when administered by the oral route.

Vitamin C, vitamin E, and betacarotene are the most important antioxidant vitamins, which gobble the free radicals generated by pollution, cigarette smoke, sun ultraviolet rays, pesticides and other contaminants in food, water, etc. In the following description of this invention, they will be collectively termed as antioxidant vitamins.

Drugs may be administered by different methods. The various methods include oral, rectal, sublingual or buceal, parental inhalation, topical, etc. The choice of method depends upon both convenience and necessity. Obviously, drug substances are most frequently administered orally for access to the systemic circulation by means of solid dosage forms, such as tablets and capsules. Oral administration does not always give rise to sufficiently high plasma concentrations to be effective. Some drugs are absorbed unpredictably or erratically. Patients occasionally have an absorption malfunction.

Fillers and binders comprise the bulk of the contents in vitamin tablets to which most people exhibit adverse side effects, such as headaches, rashes, hives, itching, and upset stomach, while the same vitamin doses when taken as the pure vitamin by injection without fillers or binders does not produce these side effects.

Several doctors who use vitamins in their practice, have observed many such undesirable reactions, including headache, arthritis, joint pain, chronic fatigue, depression, personality changes, gout attacks, and even chronic earaches and infection in children. It has been discovered that the allergic reactions are generally to table fillers and binders, not to the vitamins themselves (though it is recognized that pure vitamins can cause problems in excessive doses).

In clinical research, it has been confirmed that 8 to 10 percent of the tested, clinical population is allergic to corn starch and other corn products and about another 10 percent to soy products. These allergies can be sufficiently severe to produce very unpleasant symptoms when vitamin tablets using these fillers and binders are taken.

Unfortunately, we live in a world that is full of hostile forces, able to trigger the release of too many free radicals in our body. Some of the agents that actively contribute to the development are air pollution, asbestos, cigarette smoke, certain anti-cancer drugs, emotional stress, joint and tissue injuries, pesticides, drinking water, chemical contaminants, radiation, reperfusion injuries, ultraviolet light, etc.

When such factors trigger the release of too many radicals, the consequence can be disastrous. To acquire full protection, it is may be necessary to fortify the body with powerful antioxidant vitamins. The latest scientific findings from all over the world confirm the potential of the antioxidant vitamins to provide health benefits which may include the following:

increased protection from many forms of cancer;

stronger defenses against cardiovascular disease, such as atherosclerosis, heart attacks, and strokes;

the preservation of one's eyesight through the prevention of cataracts;

a delay in the onset of premature aging;

a more powerful immune system;

a decreased risk of early Parkinson's disease and other chronic diseases, as well as a host of other major health advantages.

Many physicians have been taking antioxidant vitamins for years, even before the weight of scientific authority shifted so heavily in the antioxidant direction.

The new paradigm in health promotion is to prevent chronic disease through lifetime health habits, including daily intakes of antioxidant vitamins. Cancer has a long latency period, and it has been estimated that the interval between the initiation of lung cancer and its eventual diagnosis is in the range of 8 to 20 years. Important studies that further solidity the connections between cancer, free radicals, and antioxidant vitamins continue to proliferate.

Cigarette smoking is known to alter components of the body's immune systems. When the body is invaded by a substance that it recognizes as "foreign," the body's immune system reacts by creating antibodies to attack the foreign substance. This response may occur locally (at a specific organ site) or systematically (throughout the body).

The body's respiratory system has a well-defined local defense system. First, there are two ciliated cells with tiny hairs that line the respiratory system. The cilia prevent accumulation of inhaled matter in the lungs by transporting the particles away from the lungs. If the cilia are rendered ineffective by smoke or other irritants, cells called macrophages take up their work by engulfing and digesting hazardous substance such as bacteria.

Experiments have been able to demonstrate clearly a decrease of the cilia action due to cigarette smoking. It has been determined that smokers have more macrophages in their lungs than nonsmokers, which may indicate the irritation of the cilia, perhaps in response to the toxic ingredients of cigarette smoke.

Studies of systemic immunological responses have shown that cigarette smoking may decrease the body's production of antibodies, thus increasing its susceptibility to infection. The influence of flu-like illness has been shown to be greater among smokers of more than half a pack a day than among nonsmokers. In addition, pregnant women who smoke have more urinary tract infections than those who do not smoke.

Although the mortality risk for people who stop smoking declines, even 15 years later it is higher than in people who had never smoked. Success in response to public health education is more likely in professional and managerial people and in those best able to understand the risks associated with smoking. Unfortunately, most smokers do not usually stop smoking until the onset of ill health.

The gaseous components found in fresh smoke of medical importance may be separated as follows:

1. Carcinogens and co-carcinogens are present in the tar. Carcinogens (principally polycyclic aromatic alcohols) initiate cancer formation. Co-carcinogens (including phenols, fatty acids, and free fatty acids) accelerate the production of cancer by other initiators. Many co-carcinogens are also irritants.
2. Irritants cause immediate coughing and bronchoconstriction after smoke inhalation, inhibit cilial action in the bronchial epithelium, stimulate bronchial mucous secretion, suppress protease inhibition, and impair alveolar macrophage function.
3. Nicotine principally affects the nervous system and is probably responsible for a smoker's pharmacologic dependence on cigarettes. Nicotine indirectly affects circulation by provoking catecholamine release which causes tachycardia, increased cardiac output, vasoconstriction, and increased PB. Nicotine also increases serum free fatty acids and platelet adhesiveness, and inhibits pancreatic bicarbonate secretion.
4. Toxic gases in cigarette smoke include CO, hydrogen sulfide, hydrocyanic acid, and oxides of nitrogen. The average carboxyhemoglobin level in people smoking one pack per day is about 5 percent compared to less than 1 percent in nonsmokers. This reduces the amount of Hb available of transport and shifts to the left the Hb-dissociation curve, impairing release to the tissues.

The diseases related to smoking are the following:

1. Lung cancer. Squamous cell and small (oat) cell lung carcinomas are associated with smoking. Epidemiologic studies have shown that men who smoke more than one pack per day are about 20 times more at risk of developing lung cancer than are nonsmokers. Laboratory experiments show that tobacco smoke condensate can produce skin cancer in animals and that animals inhaling cigarette smoke may develop cancer of the larynx or lung.
2. Chronic bronchitis and emphysema deaths are also about 20 times more frequent in people who smoke heavily. Both diseases can be produced in animals exposed to cigarette smoke. Pulmonary function tests often show airflow obstruction in the small airways even before chronic expectoration develops. The adverse effect of smoking on mucociliary clearance and on the normal balance between lung proteases and their inhibitors predisposes smokers to bronchopulmonary infection and emphysema.
3. Cardiovascular diseases: Cigarette smoking accelerates atherosclerosis and may double the risk of myocardial infarction. Smoking may precipitate an anginal attack or ischemic ECG changes in patients with coronary artery disease. The risk of developing cerebrovascular disease, peripheral vascular disease, or non-cephalic aortic aneurysm is also increased in smokers.
4. Pregnancy: The mean birth weight of infants born to mothers who smoke during pregnancy is 6 oz. less than that of infants born to nonsmoking mothers. The incidence of spontaneous abortion, stillbirth, and neonatal death may also be increased in pregnant women who smoke.
5. Extrapulmonary cancers associated with cigarette smoking include cancer of the mouth, pharynx, larynx, esophagus, bladder, and pancreas.
6. Peptic (especially gastric) ulceration occurs more frequently and has a higher mortality rate in cigarette smokers than in non-smokers. In addition, the effectiveness of medical treatment for peptic ulceration is reduced and the rate of ulcer healing is slowed.
7. Other conditions: Pulmonary TB is more common in smokers, perhaps due to activation of old tuberculosis foci. Tobacco amblyopia may be caused by optic nerve damage due to the toxic action of cyanides in cigarette smoke in smokers with vitamin deficiency.

It has been estimated by the U.S. Surgeon General that in the U.S. alone, about 500,000 deaths are caused each year by diseases related to tobacco smoking. In fact, excessive smoking is now recognized as one of the major health problems throughout the world. The most important risk factors, however, are toxic substances which are formed during the combustion of tobacco, such as carbon monoxide, tar products, aldehydes, hydrocyanic acid, etc. Nearly 1,000 constituents of tobacco smoke have been identified; many are irritants, toxic gases, or carcinogens. These particles are inhales into the lungs, where they irritate the respiratory passages and increase the production of bronchial mucous, possibly initiating cancer.

Recent discoveries about vitamin substances have caused great optimism in the search for allies in the fight against cancer, the most important, and particularly effective for the prevention and/or treatment of smoke related diseases are the antioxidant vitamins.

Antioxidant vitamins offer some protection against lung cancer and cancer of the esophagus. They may also help ward off colon, rectal, bladder, prostate, breast, cervical, larynx, gastrointestinal, and skin cancers, among others. The evidence to support these claims comes from worldwide studies of populations with diets full of food rich in vitamin C, vitamin E, and betacarotene, as well as from laboratory studies of the vitamins, ability to prevent cancers in experimental animals.

Antioxidant vitamins appear to have such powerful anti-cancer effects that the cancer establishment has started clinical trials for its use in the treatment of cancer, as well as for its prevention. Such prevention seems to be particularly effective in the case of bronchogenic squamous carcinoma, since the latter has a long latency period during which metaplasia slowly develops.

Surveys conducted in the U.S. and several European Universities revealed that smokers with diets deficient in antioxidant vitamins had twice as much lung cancer as smokers whose antioxidant vitamins intake was not deficient. At first, these patients were treated with high doses of antioxidant vitamins, but they suffered from side effects of this therapy before any effect on their cancer could be documented. When researchers started experimenting with betacarotene and retinoic acid derivatives, they found these compounds to be stronger and less toxic for cancer treatment.

Many studies, undertaken to observe the relationship between cancer and the consumption of antioxidant vitamins have shown that cancer patients have very low blood levels of antioxidant vitamins. The result of this antioxidant vitamins deficiency also provides additional clues to how and why these nutrients prevent cancer.

Antioxidant vitamins deficiency can:

cause a drop in the number of T-cells, which are required to kill any cancer cells that may arise;

result in lower levels of antibody production (normal antibody responses are necessary for healthier immunity);

enhance the ability of a carcinogen in tobacco, benzo(a) pyrene, to bind to lung cells, increasing the possibility of cancer;

cause abnormal changes in epithelial tissues (those that line the inner and outer surfaces of the body and its organs).

The first two points underline antioxidant vitamins' importance to cancer immunity. The third point tells us that antioxidant vitamins are needed to block the effect of tobacco smoke in the lungs. The fourth point is especially important to the betacarotene cancer connection. Vitamin A is required normally for the proper growth and differentiation of all epithelial tissues. The changes that can occur in these tissues, when antioxidant vitamins are low or absent, may presage cancer. Epithelial cancers make up more than half the total cancers in men and women, and occur at a wide variety of sites in the body: skin, larynx, esophagus, cervix, colon, rectum, stomach, bladder, kidney, thyroid, breast, uterus, gall bladder, and prostate. These are many of the same cancers shown in population studies to be prevented by a healthy intake of antioxidant vitamins.

Antioxidant vitamins have proven to be able to prevent chemical and spontaneous carcinogenesis in the epithelial tissue of the bronchi, trachea, stomach, skin, uterus, and prostate in man and in animals, both in vitro and in vivo. Various mechanisms have been suggested to explain these anticarcinogenic effects, and epidemiologic studies are currently testing the relationship between retinoid/carotenoid and cancer, in cancer patents and matched controls.

For several years, both the National Cancer Institute and the American Cancer Society have been recommending the use of betacarotene, vitamin A, and vitamin C supplement as a means for cancer prevention. Recent research suggest that antioxidant vitamins inhibit the cancer-causing action of tumor promoters and tumor initiators. Furthermore, in laboratory experiments, betacarotene, vitamin C, and vitamin E have been shown to transform cancer cells to cells that resemble normal cells.

The effect has been noted with tumors such as lung cancer, prostate cancer, colon cancer, and neuroblastoma (a tumor of embryonic nerve cells). In a German study published in Nutritional Abstracts and Reviews, 218 cancer patients received large amounts of antioxidant vitamins for approximately three to seven months. Tumor growth generally stopped or regressed with no side effects.

Recent discoveries about antioxidant vitamins have caused great optimism in the search for allies in the fight against cancer. No other single nutrient has excited cancer scientists quite as much. Due to their free radical scavenging effect, it is believed that antioxidant vitamins enable the body to convert carcinogens to non-toxic derivations which are eliminated in the urine and, consequently, ameliorate the effects of smoking exposure to the body. Consequently, there is little scientific doubt that the establishment and maintenance of effective levels of antioxidant vitamins in the human body yield important health advantages.

The determination of quantitative daily human requirements for antioxidant vitamins could be made if it were possible to correlate known nutrient intake with specific biological responses in precisely controlled studies. Research has also indicated that the taking of larger amounts of antioxidants than the official Recommended Daily Allowance (RDA) builds a stronger protection against free radicals. This larger amount has been suggested to as:

Betacarotene—25,000–50,000 International Units=15/30 mg.

Vitamin C—500–1,000 mg.

Vitamin E Acetate—400–800 I.U.=400/800 mg.

Though the benefits of antioxidant vitamins is well documented, methods of delivering the vitamins to the respiratory area of a patient have been far from superior. Thus, what is needed in the art is method for dispensing antioxidant vitamins within a patient which will allow for maximum benefits from such antioxidant vitamins for therapeutic treatment of diseases of the respiratory tract. It is therefore, to the effective resolution of the aforementioned problems and shortcomings that the present invention is directed.

SUMMARY OF THE INVENTION

The invention relates to a medical procedure for dispensing one or more known antioxidants and/or vitamins, such as betacarotene, vitamin C, vitamin E, and lactose in dry, powdered form by inhalation as prevention or for medical treatment for smoking related diseases. Preferably, the antioxidant(s) are in a dry, ultra silky, micro, fine powdered form. Many ingredients can be added as membrane permeation enhancers to the antioxidant vitamins formulation to increase their barrier permeability, but the preferred one and the most effective is lactose.

The present invention method delivers the dry, micro fine powder in one step and without the aid or use of aerosols, liquids, vapors, gases, vaporization or any other similar or like devices or delivery methods.

Preferably, the dry fine powder compound consist of a plurality of particles which are between 0.5 micrometer and 1 micrometer in size.

The principal purpose of the present invention is to use any inhaler known in the art to dispense a dry, powdered compound consisting of betacarotene, vitamin C, vitamin E, and lactose through the mucosal linings of tracheobronchial tree and the lungs, to prevent or cure cancer and other respiratory diseases.

The invention relates to a novel method of supplementing, through the respiratory tract, essential antioxidant vitamins by the use of a drug powder inhaler which allows their immediate assimilation, compensating for certain absorptive disorders and side effects.

Selected essential antioxidant vitamins, when administered through the respiratory tract, are directly available for absorption into the system without competition from other medications. When the antioxidant vitamins are dispersed by inhalation through the respiratory tract, they are instantaneously assimilated by the plasma and are immune to possible deterioration or interaction of prescribed medicaments and aspirin and/or alcohol.

In recent years, a great deal of scientific literature has been published, reporting the extraordinary effects of antioxidant vitamins. It is not easy to summarize in a few pages the numerous properties of these remarkable substances, the evidence accumulated to date including the studies of the present invention, leave little doubt that the antioxidant vitamins exert favorable effects on many types of cancers and, in fact, there is published evidence demonstrating that the antioxidant vitamins exert a direct topical effect on preventing the formation of tumors in respiratory tract mucosa.

Thus, it is an object of the invention to provide a composition and method for selectively supplementing the essential antioxidant vitamins in the diet of people and for facilitating its absorption for the prevention of respiratory diseases.

It is also an object of the invention to correct the deficiency of antioxidant vitamins in people due to the excessive free radicals activity which pose one of the greatest single threats to the public health and to prevent and/or eliminate the symptoms of those deficiencies. By so doing, deficiencies can be therapeutically eliminated without the need for massive doses of drugs.

A further object of the invention is to administer antioxidant vitamins in a dry, powdered form by inhalation as a prevention means or as a medical treatment.

In accordance with these and other objects which will become apparent hereinafter, the instant invention will now be described with particular reference to the accompanying drawings.

DESCRIPTION OF THE PREFERRED EMBODIMENTS

The present invention relates to employing inhalation for delivering gaseous or volatile substances into systemic circulation via the respiratory tract. Absorption is virtually as rapid as the drug can be delivered into the alveoli of the lungs, since the alveolar and vascular epithelial membranes are quite permeable, blood flow is abundant and there is a very large surface for adsorption.

Aerosol delivered from pressure-packaged, metered-dose inhalers (MDIs) are composed of the drug, additives, and propellants. The high vapor pressure of propellant supplies the force necessary to generate aerosol droplets.

Aerosol of non-volatile substances may also be administered by inhalation, but the route is infrequently used for delivery into the systemic circulation because of various factors that contribute to erratic or difficult-to-achieve blood levels. Whether or not an aerosol reaches and is retained in pulmonary alveoli depends crucially upon particle size; particles greater than 1 micrometer in diameter tend to settle in the bronchiolus and bronchi, whereas particles less than 0.5 micrometer fail to settle and are mainly exhaled. Aerosols are mostly employed when the purpose of administration is an action of the drug upon the respiratory tract itself.

Dry powder inhalers (DPIs) deliver their dose on the breath of the patient, consequently, the pattern of delivery is different from that of the metered dose inhalers. The DPI is extremely simple and foolproof, especially with respect to accuracy of dosage and accurate placement of the drug. For this reason, the DPIs are ideal vehicles to dispense vitamins to the respiratory tract, and are preferable to the aerosol inhaler, particularly over oral preparations for several reasons. An example of a dry powder inhaler which can be utilized to deliver the dose of dry powder antioxidant composition is shown in my co-pending application U.S. patent application Ser. No. 08/576,816 which is incorporated herein by reference. Other conventional dry powder inhaler may also be utilized and are considered within the scope of the invention.

After a drug is swallowed, it is absorbed into the bloodstream, returned to the heart, and then pumped to all organs in the body. One must take a relatively large amount of an oral drug to deliver a small dose to a selected target organ, such as the lungs. The drug is also transported to other organs where it is not needed and may cause unwanted side effects. The shortcomings of oral drugs are overcome by the present invention which delivered a drug or vitamin directly to the target organ. Thus, the present invention provides a method for dispensing a dry, powdered compound consisting of vitamin C, vitamin E, betacarotene, and lactose using a DPI, which can be inhaled into the lungs to produce a faster onset of action without any side effects. This new method of dispensing antioxidant vitamins through the respiratory tract is breath-activated, meaning the patient does not have to coordinate inhalation with activating the inhaler and does not inhale cardiotoxic gas propellants into the lung.

The lung is considered to be one of the more effective non-invasive routes of administration to the systemic circulation. A number of dry, powder vitamins can be used to treat a variety of conditions that accompany many different diseases and to neutralize toxic and carcinogenic effects of the harmful ingredients in tobacco smoke.

Antioxidant vitamins may reverse precancerous change, and it has been shown that the abnormalities seem to return when the preventive administration of antioxidant vitamins is discontinued. In some cases, the antioxidant vitamins delay the onset of cancer, as they may double the time it takes for a cancer to develop.

The antioxidant vitamins are the body's most important antioxidant. They protect the body from the damaging effects of uncontrolled oxidation and free radicals. This uncontrolled oxidation can cause cancer, induce abnormal blood clots, resulting in stroke or heart attack, and damage the DNA in our cells which control growth, stimulate the immune system, and prevent and repair ultraviolet light damage.

Large doses of antioxidant vitamins have been shown to increase resistance to cancer, bacterial and viral infections, stroke, arthritis, heart attack, and protect against the effects of many pollutants.

In recent years, much scientific research has been done and the validity of using antioxidant vitamins, such as vitamin C, vitamin E, and betacarotene to prevent and/or cure diseases and to bolster the immune defenses against excessive numbers of free radicals, due to their powerful antioxidant property, have been proven.

The method of application of the present invention makes possible delivering the antioxidant vitamins into the respiratory tract of humans in order to enhance the prophylactic and therapeutic effects of such vitamins to decrease the risk of cancer smokers. Thus, dispensing such antioxidant vitamins into the respiratory tract before, during, or after smoking, in accordance with our numerous laboratory tests, we have been successful in confirming vitamins specific preventive effects in the development of cancer.

Accordingly, one purpose of this invention is to provide a dry, powder compound of antioxidant vitamins for local administration by inhalation. This system offers the advantages of (1) local administration of small doses of the above antioxidant vitamins with protective effect against bronchial carcinogenesis in a "non-pharmacological" and spontaneous way; and (2) concomitant distribution of such antioxidant vitamins in the respiratory tract of smokers, which are more effectively absorbed and retained in the human body with specific preventive effect.

While the present invention has been described with reference to specific medical procedure for dispensing antioxidant vitamins by inhalation, it will be understood by those skilled in this art that various other antioxidants vitamins can be used without departing from the spirit of the invention. Such antioxidants comprise: Coenzyme Q-10 (Ubiquinone), SOD (Superoxide Dismutase), Catalase, GSH (Glutathhione Peroxidase), Selenium, Alpha Lipoic Acid, Pychogenol, etc., and rights to such alternatives are particularly reserved, especially those which fall within the scope of the appended claims.

Thus, in use a mixture of preferably vitamin C, vitamin E, betacarotene and a membrane permeation enhancer such as lactose, is formed into a dry powder compound and kept together, prior to use, by conventional means, such as a capsule member. The capsule member, containing the dry powder compound is disposed into a conventional dry powder inhaler. When the dry powder compound is desired, the inhaler is activated causing the compound to be delivered to the subject's respiratory tract in order to enhance prophylactic and therapeutic effects of the antioxidant vitamins. Other antioxidant vitamins can also be included within the dry powder compound. Thus, the dry powdered compound is inhaled into the subject's lungs to produce a faster onset of action. When administered through the respiratory tract, the antioxidant vitamins are directly available for absorption into the subject's system without competition from other medications. When the antioxidant vitamins are dispersed by inhalation through the respiratory tract, they are instantaneously assimilated by the plasma and are immune to possible deterioration or interaction of prescribed medicaments and aspirin and/or alcohol.

The present invention method delivers the dry, micro fine powder in one step and without the aid or use of aerosols, gases, liquids, vaporization or any other similar or like devices or methods.

Preferably, the antioxidant vitamins are in a dry, ultra silky, micro fine powdered form. The dry powder compound preferably consist of a plurality of particles which are between 0.5 micrometer and 1 micrometer in size.

The instant invention has been shown and described herein in what is considered to be the most practical and preferred embodiment. It is recognized, however, that departures may be made therefrom within the scope of the invention and that obvious modifications will occur to a person skilled in the art.

What I claim is:

1. A method for dispensing one or more antioxidants in the form of a dry micro fine powder directly to a human subject by inhalation, said method comprising the steps of:
   (a) forming a dry micro fine powder composition comprising at least one antioxidant; and
   (b) dispensing, upon breath activation by the human subject, of an effective amount of the dry micro fine powder antioxidant composition directly into the mouth of the subject by a dry powder inhaler, without the use of gas(es), liquids, aerosol(s) or vaporization, to allow said composition to reach the subject's respiratory tract.

2. The method for dispensing of claim 1 wherein said dry micro fine powder composition further consist of a membrane permeation enhancer.

3. The method for dispensing of claim 2 wherein said membrane permeation enhancer is preferably lactose.

4. The method for dispensing of claim 1 wherein said method allows for delivery of said at least one antioxidant into the subject's respiratory tract in order to enhance prophylactic and therapeutic effects of said at least one antioxidant vitamin.

5. A method for dispensing one or more antioxidants in a dry micro fine powder form directly to a human subject with the use of a conventional dry powder inhaler, said method comprising the steps of:
   (a) forming a dry micro fine powder composition comprising at least one antioxidant with or without a membrane permeation enhancer; and
   (b) dispensing, upon breath activation by the human subject, of an effective amount of the dry micro fine powder composition directly into the mouth of the subject with the dry powder inhaler to allow said composition to reach the subject's respiratory tract, without the use of gas(es), liquids, aerosol(s) or vaporization.

6. The method for dispensing of claim 5 wherein said method allows for delivery of said at least one antioxidant into the subject's respiratory tract in order to enhance prophylactic and therapeutic effects of said at least one antioxidant.

7. The method for dispensing of claim 5 wherein said membrane permeation enhancer is preferably lactose.

8. A method for improving the effectiveness of one or more antioxidants when administered to a human subject, said one or more antioxidants in a dry micro fine powder form, said method comprising the step of administering to a subject an effective dose of a dry micro fine powder composition of at least one antioxidant, with or without lactose, via a conventional dry powder inhaler, upon breath activation by the human subject, to deliver said at least one antioxidant directly into the subject's respiratory tract, without the use of gas(es), liquids, aerosol(s) or vaporization, in order to enhance prophylactic and therapeutic effects of said at least one antioxidant.

9. The method of claim 8 wherein said at least one antioxidant is Vitamin C.

10. The method of claim 8 wherein said at least one antioxidant is Vitamin E.

11. The method of claim 8 wherein said at least one antioxidant is betacarotene.

12. The method of claim 8 wherein said at least one antioxidant is a compound of Vitamin C, Vitamin E and betacarotene.

13. The method of claim 8 wherein said dry micro fine powder compound consist of a plurality of particles which are between 0.5 micrometer and 1 micrometer in size.

* * * * *